United States Patent [19]

Trowell

[11] Patent Number: 4,720,571

[45] Date of Patent: Jan. 19, 1988

[54] POLYOLS FROM SCRAP POLYETHYLENE TEREPHTHALATE AND DIMETHYL TEREPHTHALATE PROCESS RESIDUE

[75] Inventor: John M. Trowell, St. Simons Island, Ga.

[73] Assignee: Hercules Incorporated, Wilmington, Del.

[21] Appl. No.: 875,831

[22] Filed: Jun. 18, 1986

[51] Int. Cl.$^4$ .................... C07C 69/82; C07C 67/03
[52] U.S. Cl. ........................... 560/91; 521/131; 521/159; 521/172; 521/173; 560/89; 560/92; 252/182
[58] Field of Search .............. 560/89, 91, 92; 252/182; 521/131, 159, 172, 173

[56] References Cited

U.S. PATENT DOCUMENTS

| | | | |
|---|---|---|---|
| 3,647,759 | 3/1972 | Walker | 521/172 |
| 4,048,104 | 9/1977 | Svoboda et al. | 521/172 |
| 4,223,068 | 9/1980 | Carlstrom et al. | 428/310 |
| 4,346,229 | 8/1982 | Derr et al. | 560/91 |
| 4,411,949 | 10/1983 | Snider et al. | 428/304.4 |
| 4,439,550 | 3/1984 | Brennan | 521/131 |
| 4,439,551 | 3/1984 | Yeakey et al. | 252/182 X |
| 4,444,918 | 4/1984 | Brennan | 521/131 |
| 4,444,920 | 4/1984 | Brennan | 521/173 |
| 4,469,824 | 9/1984 | Grigsby, Jr. et al. | 521/173 |
| 4,506,090 | 3/1985 | Brennan et al. | 560/91 |

FOREIGN PATENT DOCUMENTS 93247 11/1983 European Pat. Off.

*Primary Examiner*—Howard T. Mars
*Assistant Examiner*—Vera C. Clarke
*Attorney, Agent, or Firm*—Joanne W. Patterson

[57] ABSTRACT

Disclosed is a mixture of terephthalic acid ester polyols for use in the preparation of rigid polyurethane and polyisocyanurate foams. The polyols are prepared by reacting scrap polyethylene terephthalate, dimethyl terephthalate process residue and an excess of a mixture of glycols.

18 Claims, No Drawings

POLYOLS FROM SCRAP POLYETHYLENE TEREPHTHALATE AND DIMETHYL TEREPHTHALATE PROCESS RESIDUE

FIELD OF THE INVENTION

This invention relates to liquid terephthalate acid ester polyols for use in the preparation of rigid polyurethane and polyisocyanurate foams. This invention especially relates to polyols produced by reacting scrap polyethylene terephthalate, dimethyl terephthalate process residue and an excess of a mixture of glycols.

BACKGROUND OF THE INVENTION

It is known to prepare rigid polyurethane (PUR) and polyisocyanurate (PIR) foams by the reaction of a polyisocyanate, a polyol and a blowing agent in the presence of a catalyst. A wide variety of polyols have been used as one of the components in preparing rigid foams, including polyols made from scrap polyethylene terephthalate or from dimethyl terephthalate process residue.

The use of scrap polyethylene terephthalate (PET), also referred to in the art as recycled PET, for the preparation of rigid polyurethane foams is described, for example, in U.S. Pat. No. 4,439,550 and U.S. Pat. No. 4,439,551. These patents disclose that a mixture of aromatic polyols for use in preparing rigid foams can be prepared by transesterifying recycled PET with the reaction product of a residue from dibasic acid manufacture and an alkylene glycol. U.S. Pat. No. 4,469,824 describes the preparation of a mixture of liquid terephthalic ester polyols produced by reacting recycled polyethylene terephthalate with diethylene glycol and at least one more oxyalkylene glycol, and stripping out some of the ethylene glycol present. These polyols are useful as extenders in rigid polyurethane foams and as the sole polyol component in polyisocyanurate foams. A mixture of aromatic polyols prepared by transesterifying recycled polyethylene terephthalate with the reaction product of an aromatic carbonyl-containing compound and an alkylene glycol is described in U.S. Pat No. 4,506,090.

The use of by-products produced in the manufacture of dimethyl terephthalate (DMT) as the polyol component in polyisocyanurate foams is described, for example, in U.S. Pat. No. 4,411,949. In this patent a polyol mixture is obtained by transesterifying a by-product fraction from the manufacture of dimethyl terephthalate with a glycol. U.S. Pat. No. 4,346,229 discloses the product produced by reacting DMT process residue with dipropylene glycol or a mixture of glycols. In U.S. Pat. No. 4,444,918 a terephthalic ester waste stream from the manufacture of PET or DMT is transesterified with the reaction product of a residue from dibasic acid manufacture and an alkylene glycol to produce polyols for rigid foams. U.S. Pat. No. 4,444,920 relates to a mixture of aromatic polyols, suitable for use in rigid foams, prepared by reacting a DMT waste stream over a metal alkoxide catalyst and then transesterifying the product with a polyalkylene glycol.

Presently available polyols made from scrap PET or DMT process residue suffer from a variety of disadvantages such as the settling of solids from solution upon standing and lack of compatibility with the fluorocarbon blowing agents commonly used in the manufacture of rigid foams. Foams prepared from these polyols are sometimes deficient in compressive strength or in flame resistance or both.

SUMMARY OF THE INVENTION

It has now been found that rigid polyurethane and polyisocyanurate foams with improved properties can be prepared from a mixture of terephthalic acid ester polyols that has a high aromatic content and is compatibile with fluorocarbon blowing agents.

The mixture of liquid terephthalic acid ester polyols of this invention is free from solids upon standing for a prolonged period of time and is prepared by (a) reacting a mixture comprised of scrap polyethylene terephthalate, dimethyl terephthalate process residue and at least two glycols having a molecular weight higher than that of ethylene glycol, in the presence of an esterification/transesterification catalyst, where the mole ratio of glycols to scrap PET and DMT process residue is from about 2:1 to about 6.5:1 and the mole ratio of scrap polyethylene terephthalate to dimethyl terephthalate process residue is from about 95/5 to about 50/50, to yield a reaction product comprising terephthalic acid ester polyols, ethylene glycol and unreacted glycols having a molecular weight greater than that of ethylene glycol, and (b) subsequently removing glycols from the reaction product from step (a) until from about 2% to about 25% glycols are present in said reaction product. Methyl-alpha-d-glucoside (MG), also referred to in the art as methyl glucoside or alpha-methyl glucoside, may also be used as one of the reactants in the production of the polyols.

DETAILED DESCRIPTION OF THE INVENTION

The mixture of liquid terephthalic acid ester polyols of this invention is prepared by a two step process. In the first step, the simultaneous esterification/transesterification of the DMT process residue and glycolysis of the PET with an excess of a mixture of glycols, and, optionally, methyl glucoside, is allowed to proceed initially at 150°–250° C. while continuously removing the water and methanol that are generated. When the evolution of methanol and water essentially ceases, the reactor is kept on partial reflux until the glycolysis of the PET reaches equilibrium. The product from the first step contains terephthalic acid ester polyols, ethylene glycol from the PET and any glycols that are not used up in the esterification/transesterification and glycolysis reactions. In the second step, the reactor is cooled to 150°–200° C. and the reaction product is filtered. A portion of the excess glycols is then removed from the filtrate to prevent precipitation of solids during storage of the polyols.

By scrap PET is meant waste or scrap PET that has already been used in another form and discarded. The scrap PET may be in any particulate form. A frequently seen form is fragmented PET soft drink bottles which can be either clear or colored. Scrap polyethylene terephthalate film and fiber can also be used. If the PET source is fiber resin scrap containing $TiO_2$ brightening agent, a suitable filter aid such as Celite 545, a diatomaceous earth filter aid manufactured by Fisher Scientific Company, is used during the filtration of the reaction product. The filter aid removes the slight haze imparted by the $TiO_2$ While scrap PET is preferred for economic reasons, it should be understood that any form of PET can be used.

The residue from the manufacture of dimethyl terephthalate (DMT) is a tar-like, solid material composed of a highly complex mixture of high molecular weight monomeric and polymeric constituents, included among which are the methyl and benzyl esters of biphenyl and triphenyl dicarboxylic and tricarboxylic acids. The high aromatic content of the residue contributes to the improved flame resistance, dimensional stability and compressive strength of foams made from the polyols of this invention. The residue at 25° C. has the following typical ranges of properties:

| Color | Dark Brown |
|---|---|
| Drop Softening Point[1] | 10-140° C. |
| Acid Number (ASTM D1639, neutral chloroform solvent) | 10-110 |
| Methoxyl in COOCH$_3$ (ASTM D-1166-60) | 7-30% by weight |
| DMT | 0-20% by weight |
| Saponification Number[2] | 375-500 |

[1]Hercules drop softening point method as described on page 12 of a booklet entitled "Wood Rosins, Modified Rosins and Related Resins", published in 1963 by Hercules Powder Company now by change of name Hercules Incorporated.
[2]Anal. Chem. 23, 1126 (1951)

Polyester polyols with properties that are satisfactory for urethane and isocyanurate foam formulations can be obtained at a charge ratio of glycols to a mixture of scrap PET and DMT process residue of from about 2.0 to about 6.5 moles glycol/mole DMT process residue and repeating unit of PET. A repeating unit of PET has a molecular weight of 192 g. Hereafter this repeating unit is referred to as a mole of PET. The preferred charge ratio is about 3.6. At lower charge ratios the viscosity of the final product increases and the % ethylene glycol recovered compared with the amount of PET charged decreases.

A mixture of at least two glycols having a molecular weight higher than that of ethylene glycol is used for the esterification/transesterification of the DMT process residue and the glycolysis of the scrap PET. A mixture of diethylene glycol and dipropylene glycol is preferred. A commercially available crude dipropylene glycol stream containing approximately 80% dipropylene glycol and 20% tripropylene glycol, hereinafter referred to as crude dipropylene glycol, can be used as the source of dipropylene glycol.

The glycol mixtures used are preferably about 60/40 diethylene glycol/crude dipropylene glycol for the process in which no methyl glucoside is present and 70/30 when methyl glucoside is one of the reactants. The ratio of PET to DMT process residue can be varied from about 95/5 to about 50/50. The preferred ratio of PET to DMT process residue is about 70/30, with or without methyl glucoside.

Any catalyst suitable for esterification or transesterification reactions can be used in the process of this invention. Such catalysts are well known in the art. Zinc oxide is preferred.

An important feature of the process for making the polyol mixtures of this invention is the removal of excess glycols, including ethylene glycol, that are present in the product from the first step of the process. The ethylene glycol is derived from the PET during the reaction and contributes to the creation of solids which tend to precipitate out when the polyol mixtures are left standing for a prolonged period of time. Glycols in an amount corresponding to from about 25% to about 60% by weight of the reaction product from the first step of the process, preferably 40-45%, should be removed. Of the glycols removed, 4.5-15%, preferably about 10%, is ethylene glycol. The excess glycols can be removed by any method known to the art. The preferred method is vacuum stripping whereby the glycols are removed as an overhead fraction at less than 10 mm Hg vacuum. The final product, the mixture of liquid terephthalic acid ester polyols, contains 2-25% free glycols.

The process is carried out at a temperature of from about 150° to about 250° C. The process is typically carried out at atmospheric pressure. However, it will be obvious to those skilled in the art that pressures higher than atmospheric can be used. At higher pressures the reaction temperature can be increased significantly, thus shortening the reaction time.

For use in the manufacture of PUR and PIR foams, the polyols of this invention preferably have a hydroxyl number in the range of 240 to 500, most preferably about 340.

The functionality of the polyol product and the dimensional stability of foams produced from it can be increased by including a polyhydric alcohol such as pentaerthyritol, glycerin or methyl glucoside in the reaction mixture. Methyl glucoside is preferred. When a polyhydric alcohol is used, it is present in an amount of from about 0.1 to about 0.3 moles polyhydric alcohol per mole of PET and DMT process residue. When a polyhydric alcohol is present in the reaction mixture the reactor is not cooled after removing excess glycols in the second step of the process. Instead the reactor is heated to 200° C. and held at that temperature for one hour after removal of excess glycols.

The terephthalic acid ester polyols of this invention are compatible with trichlorofluoromethane, a conventional blowing agent used in the production of closed-cell rigid foams and sold under the trademark FREON 11. 30% FREON 11 solubility is considered to be 100% compatibility. 15% FREON 11 solubility is typical of commercially available aromatic polyester polyols in a neat system. The % FREON 11 solubility of the polyols of this invention is in the range of from about 19% to about 24% for the polyols prepared without methyl glucoside, and from about 16% to about 18% for the polyols prepared with methyl glucoside present in the reaction mixture, when the mixture of glycols used in the first step of the process is a mixture of diethylene glycol and crude dipropylene glycol. If only crude dipropylene glycol (which contains approximately 20% tripropylene glycol) is used, the FREON 11 compatibility increases to 30%, with or without methyl glucoside in the reaction mixture.

The following examples are illustrative of this invention and are not intended to limit its scope in any way. All parts and percentages in this specification are by weight unless otherwise specified.

EXAMPLE 1

Diethylene glycol (1,325 g), 884 g crude dipropylene glycol, 300 g DMT process residue and 0.62 g zinc oxide catalyst are charged to a five liter reactor. The reactor contents are heated to 150°-160° C. and 700 g PET bottle scrap are added with agitation. The temperature of the reactor is increased to 220° C. and methanol and water are distilled overhead and collected. When it is no longer possible to control the overhead temperature to less than 110°-115° C., the reactor is kept on partial reflux at 100° C., anything boiling higher than 100° C. being returned to the reactor. A sample is then removed from the reactor and analyzed for glycols. The sampling and analysis are repeated every hour until two consecutive analyses are essentially identical, indicating that glycolysis of the PET has reached equilibrium.

The reactor is then cooled to 150°-200° C. and the product is filtered using a centrifuge. The filter paper retains particles 10 microns in diameter or larger.

The filtrate is returned to the reactor and glycols are removed by vacuum stripping at 3 mm Hg and a maximum reactor temperature of 140° C. Samples are removed periodically from the reactor during the vacuum stripping and analyzed for free glycols. When the glycol concentration reaches 14.8%, the reactor is cooled and the contents transferred to a suitable storage container. Details of the reaction cycle and the properties of the final product are given in the table below.

EXAMPLE 2

Diethylene glycol (1,172 g), 501 g crude dipropylene glycol, 255 g DMT process residue and 0.53 g zinc oxide catalyst are charged to a five liter reactor. The reactor contents are heated to 150°-160° and 201 g methyl alpha-d-glucoside and 595 g PET bottle scrap are added with agitation. The remainder of the reaction cycle and the vacuum stripping process are identical to those described in Example 1 except that the reactor is not cooled after stripping off excess glycols. Instead the reactor is heated to 200° C. and maintained at that temperature for one hour after stripping. Details of the reaction cycle and the properties of the final product are given in the table.

EXAMPLE 3-6

The polyols of Examples 3 and 6 are prepared as described in Example 1. The polyols of Examples 4 and 5 are prepared as described in Example 2. Details of the reaction cycle and the properties of the final product are given in the table.

(a) reacting a mixture comprised of scrap polyethylene terephthalate, dimethyl terephthalate process residue and at least two glycols having a molecular weight higher than that of ethylene glycol, in the presence of an esterification/transesterification catalyst, where the mole ratio of glycols to scrap polyethylene terephthalate and dimethyl terephthalate process residue is from about 2:1 to about 6.5:1 and the mole ratio of scrap polyethylene terephthalate to dimethyl terephthalate process residue is from about 96/5 to about 50/50, to yield a reaction product comprising terephthalic acid ester polyols, ethylene glycol and unreacted glycols having a molecular weight higher than that of ethylene glycol, and (b) subsequently removing glycols from the reaction product from step (a) until from about 2% to about 25% by weight glycols are present in said reaction product.

2. The mixture of polyols of claim 1 wherein the glycols having a molecular weight higher than that of ethylene glycol are a mixture of diethylene glycol, dipropylene glycol and tripropylene glycol.

3. The mixture of polyols of claim 1 wherein the reaction mixture of step (a) additionally comprises from about 0.1 to about 0.3 moles methyl alpha-d-glucoside per mole of scrap polyethylene terephthalate and dimethyl terephthalate process residue.

4. The mixture of polyols of claim 1 wherein removal of glycols from the reaction product from step (a) is accomplished by vacuum stripping.

5. The mixture of polyols of claim 1 wherein the reaction is conducted at a temperature of 150°-250° C.

6. The mixture of polyols of claim 1 wherein the reaction is conducted at atmospheric pressure.

7. The mixture of polyols of claim 1 wherein the esterification/transesterification catalyst is zinc oxide.

8. The mixture of polyols of claim 1 wherein the

|  | Example 1 | Example 2 | Example 3 | Example 4 | Example 5 | Example 6 |
|---|---|---|---|---|---|---|
| Ratio PET/DMT residue | 70/30 | 70/30 | 90/10 | 95/5 | 70/30 | 90/10 |
| Charge Ratio, |  |  |  |  |  |  |
| Moles Glycol/Mole PET & DMT Residue | 3.96 | 3.88 | 3.62 | 6.15 | 5.76 | 2.90 |
| Moles MG/Mole PET & DMT Residue | 0 | 0.26 | 0 | 0.23 | 0.26 | 0 |
| Glycol Concentration, % @ Equilibrium |  |  |  |  |  |  |
| EG | 3.78 | 3.33 | 4.94 | 3.70 | 2.68 | 5.24 |
| DEG | 26.1 | 25.8 | 25.5 | 39.0 | 35.2 | 18.2 |
| DPG | 15.8 | 10.4 | 14.8 | 14.2 | 13.8 | 13.0 |
| TPG | 3.25 | 2.11 | 2.42 | — | 2.54 | 2.24 |
| Percentage of Charge Stripped Ovh. | 41 | 33 | 42 | 54 | 46 | 32 |
| Composition of Vac. Stripped Ovh's, % |  |  |  |  |  |  |
| EG | 7.70 | 8.27 | 12.1 | 7.33 | 4.85 | 13.7 |
| DEG | 52.0 | 57.3 | 49.0 | 62.8 | 61.0 | 45.8 |
| DPG | 33.7 | 26.2 | 31.8 | 25.1 | 26.5 | 33.2 |
| TPG | 3.63 | 2.97 | 3.20 | 2.92 | 3.16 | 4.97 |
| Polyol Properties |  |  |  |  |  |  |
| Hydroxyl No. | 350 | 441 | 347 | 454 | 462 | 326 |
| Glycol Free Hydroxyl No. | 250 | 350 | 258 | 378 | 358 | 242 |
| Acid No. | 3.4 | 3.8 | 1.9 | 2.1 | 4.3 | 2.1 |
| Viscosity, cps @ 25° C. | 2,500 | 5,700 | 2,000 | 3,700 | 3,200 | 4,200 |
| Water, % | 0.02 | 0.02 | 0.02 | 0.01 | 0.01 | 0.05 |
| EG, % | 0.12 | 0.05 | 0.20 | 0.01 | 0.02 | 0.34 |
| DEG, % | 9.20 | 10.7 | 8.52 | 9.92 | 12.7 | 8.00 |
| DPG, % | 3.27 | 2.38 | 2.66 | 1.34 | 2.46 | 2.65 |
| TPG, % | 2.21 | 1.57 | 1.83 | 1.39 | 1.94 | 1.22 |
| FREON 11 Solubility, % | 24 | 16 | 22 | 17 | 17 | 24 |

What I claim and desire to protect by Letters Patent is:

1. A mixture of liquid terephthalate acid ester polyols that is free from solids upon standing and is prepared by average hydroxyl number of the mixture of polyols is from about 240 to about 500.

9. The mixture of polyols of claim 1 wherein the ratio of scrap polyethylene terephthalate to dimethyl terephthalate process residue is about 70/30.

10. A process for producing a mixture of liquid terephthalic acid ester polyols that is free from solids upon standing comprising
   (a) reacting a mixture comprised of scrap polyethylene terephthalate, dimethyl terephthalate process residue and at least two glycols having a molecular weight higher than that of ethylene glycol, in the presence of an esterification/transesterification catalyst, where the mole ratio of glycols to scrap polyethylene terephthalate and dimethyl terephthalate process residue is from about 2:1 to about 6.5:1 and the mole ratio of scrap polyethylene terephthalate to dimethyl terephthalate process residue is from about 95/5 to about 50/50, to yield a reaction product comprising terephthalic acid ester polyols, ethylene glycol and unreacted glycols having a molecular weight higher than that of ethylene glycol, and
   (b) subsequently removing glycols from the reaction product from step (a) until from about 2% to about 25% by weight glycols are present in said reaction product.

11. The process of claim 10 wherein the glycols having a molecular weight higher than ethylene glycol are a mixture of diethylene glycol, dipropylene glycol and tripropylene glycol.

12. The process of claim 10 wherein the reaction mixture of step (a) additionally comprises from about 0.1 to about 0.3 moles methyl alpha-d-glucoside per mole of scrap polyethylene terephthalate and dimethyl terephthalate process residue.

13. The process of claim 10 wherein removal of glycols from the reaction product from step (a) is accomplished by vacuum stripping.

14. The process of claim 10 wherein the reaction is conducted at a temperature of 150°–250° C.

15. The process of claim 10 wherein the reaction is conducted at atmospheric pressure.

16. The process of claim 10 wherein the esterification/transesterification catalyst is zinc oxide.

17. The process of claim 10 wherein the average hydroxyl number of the mixture of polyols is from about 240 to about 500.

18. The process of claim 10 wherein the ratio of scrap polyethylene terephthalate to dimethyl terephthalate process residue is about 70/30.

* * * * *